(12) United States Patent
Johnson et al.

(10) Patent No.: US 11,236,029 B2
(45) Date of Patent: Feb. 1, 2022

(54) SYNTHESIS OF A TRIANGULENE RING SYSTEM AND DERIVATIVES THEREOF

(71) Applicant: THE UNIVERSITY OF NEW HAMPSHIRE, Durham, NH (US)

(72) Inventors: Richard Peter Johnson, Newmarket, NH (US); Carter J. Holt, Dover, NH (US)

(73) Assignee: UNIVERSITY OF NEW HAMPSHIRE, Durham, NH (US)

(*) Notice: Subject to any disclaimer, the term of this patent is extended or adjusted under 35 U.S.C. 154(b) by 0 days.

(21) Appl. No.: 16/876,582

(22) Filed: May 18, 2020

(65) Prior Publication Data

US 2021/0040019 A1 Feb. 11, 2021

Related U.S. Application Data

(60) Provisional application No. 62/849,647, filed on May 17, 2019.

(51) Int. Cl.
| | |
|---|---|
| C07C 15/20 | (2006.01) |
| C07C 41/30 | (2006.01) |
| C07C 1/24 | (2006.01) |
| C07C 29/10 | (2006.01) |
| C07F 1/02 | (2006.01) |

(52) U.S. Cl.
CPC ............ *C07C 15/20* (2013.01); *C07C 1/24* (2013.01); *C07C 29/10* (2013.01); *C07C 41/30* (2013.01); *C07F 1/02* (2013.01); *C07C 2603/22* (2017.05); *C07C 2603/54* (2017.05)

(58) Field of Classification Search
None
See application file for complete search history.

(56) References Cited

PUBLICATIONS

Ribar et al. "Supporting Information for Gram-Scale Synthesis and Supramolecular Complex of Precursors of Clar's Hydrocarbon Triangulene" Organic Letters 2019, 21, S1-S48. (Year: 2019).*

* cited by examiner

*Primary Examiner* — Philip Y Louie
*Assistant Examiner* — Alyssa L Cepluch
(74) *Attorney, Agent, or Firm* — Grossman, Tucker, Perrault & Pfleger, PLLC

(57) ABSTRACT

A three step synthesis of the 8,12-dihydro-4H-dibenzo[cd,mn]pyren-3a$^2$-ylium cation (triangulenium cation) is effected by cascade cyclization of a tetra-benzyl alcohol precursor in triflic acid solution. This cation is easily observed by NMR and optical spectroscopy. Quenching of the cation into basic solutions or by hydride transfer from triethylsilane provides access to stable dihydro and tetrahydro[3]triangulenes. This route makes several [3]triangulene precursors more readily available for development of new applications in the field of molecular electronics.

4 Claims, 3 Drawing Sheets

SYNTHESIS OF A TRIANGULENE RING SYSTEM AND DERIVATIVES THEREOF

CROSS-REFERENCE TO RELATED APPLICATION

The present application claims the benefit of the filing date of U.S. Provisional Application, Ser. No. 62/849,647, filed May 17, 2019, which is fully incorporated herein by reference.

FIELD

The present disclosure describes the synthesis of structures known as triangulenes which have unusual electronic properties and which have utility in the field of molecular electronics. This disclosure describes the synthesis of 8,12-dihydro-4H-dibenzo[cd,mn]pyren-3a$^2$-ylium cation (triangulenium cation) and its derivatives. More specifically, the reaction of a protected benzyl alcohol precursor with diethyl carbonate is followed by deprotection and formation of a tetra-benzyl alcohol precursor. Acid-catalyzed cyclization of this precursor yields the triangulenium cation, with ensuing preparation of dihydro and tetrahydrotriangulenes, one of which is a precursor to the hydrocarbon known as triangulene.

BACKGROUND

Triangular-shaped aromatic hydrocarbons comprise a homologous series of open shell structures, beginning with the well-studied phenalenyl radical (1).[1-2] See FIG. 1. Higher homologs 2 and 3 are expected to exist as di- and tri-radicals, respectively and both have been predicted to possess high spin ground states.[3-8] See again, FIG. 1. Homolog 2 is commonly known as triangulene or [3]triangulene to indicate the number of rings on one side. The systematic name for 2 is 1H,4H-dibenzo[cd,mn]pyrene-1,4-diyl.

Synthetic routes to the ring system of homolog 2 were first described by Clar in 1954[9-11] with later work reported by Bushby on trioxy derivatives.[12] The aromatic [3]triangulene dianion has been prepared from the Clar route.[13] Takui and Nakasuji reported on the synthesis and ESR spectrum of 2,6,10-tri-t-butyl triangulene[14] confirming the existence of a kinetically unstable ground state triplet. There is a growing literature predicting the chemistry of 2[15-18] and a variety of heterocyclic versions are known[19-25] but the parent hydrocarbon was only recently prepared and observed as single molecules by scanning probe microscopy.[26] At present, synthetic routes to this novel ring system are relatively lengthy (>7 steps) and suitable precursors to 2 have been prepared only in relatively small quantities.[26]

SUMMARY

A method for the preparation of 8,12-dihydro-4H-dibenzo[cd,mn]pyren-3a$^2$-ylium cation comprising reacting an allyl-protected benzyl alcohol having the following structure:

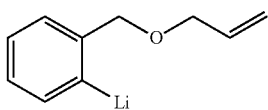

with diethyl carbonate to form tris(2-((allyloxy)methyl)phenyl)methanol having the following structure:

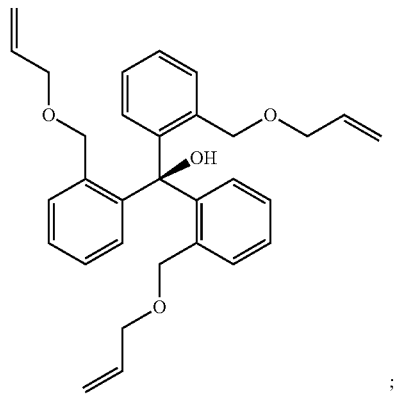

converting said tris(2-((allyloxy)methyl)phenyl)methanol to ((hydroxymethanetriyl)tris(benzene-2,1-diyl))trimethanol having the following structure:

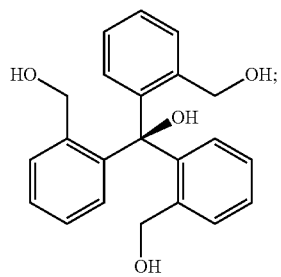

converting said ((hydroxymethanetriyl)tris(benzene-2,1-diyl))trimethanol to 8,12-dihydro-4H-dibenzo[cd,mn]pyren-3a$^2$-ylium cation having the following structure:

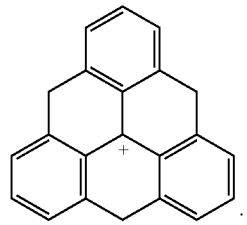 [SMILES: c1cc2c3c(c1)Cc1cccc4c1[C+]3c1c(cccc1C4)C2]

This may then be followed by converting said 8,12-dihydro-4H-dibenzo[cd,mn]pyren-3a$^2$-ylium cation to dihydro and tetrahydrotriangulenes having the following structures:

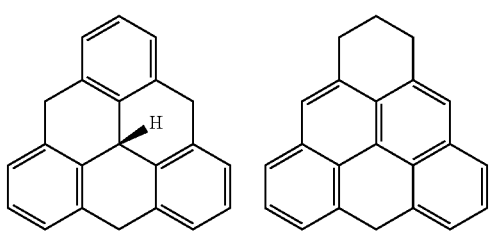

-continued

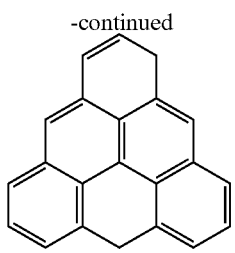

DETAILED DESCRIPTION OF THE PREFERRED EMBODIMENTS

Figure 1:
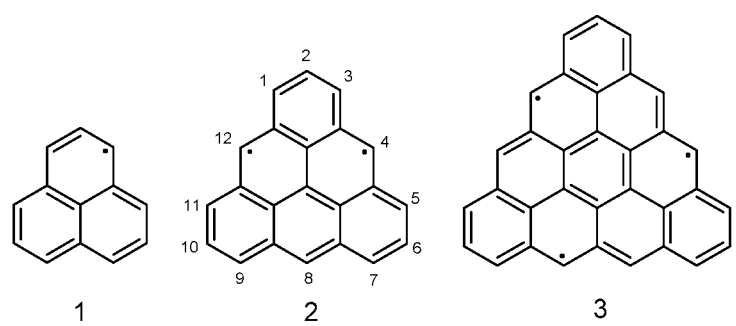
FIG. 1. Triangular-shaped aromatic hydrocarbons where 1 is the phenalenyl radical and 2 and 3 are higher homologs.
Figure 2:
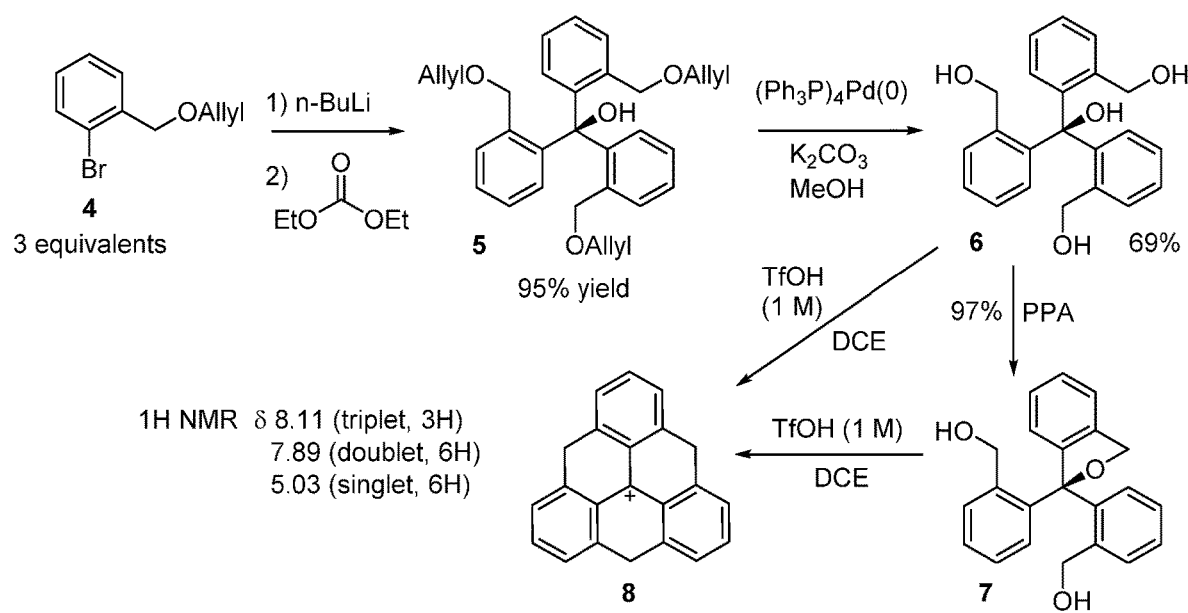
FIG. 2. Route for the preparation of the 8,12-dihydro-4H-dibenzo[cd,mn]pyren-3a²-ylium cation.

FIG. 2 summarizes the preferred route herein for the preparation of the 8,12-dihydro-4H-dibenzo[cd,mn]pyren-3a²-ylium cation. Taking advantage of the 3-fold symmetry of this structure, condensation of three equivalents of allyl protected benzyl alcohol 4 using n-butyl lithium followed by diethyl carbonate afforded tris(2-((allyloxy)methyl)phenyl) methanol 5 in a single synthetic step and relatively high yield 90%). Palladium catalyzed deprotection yielded the crystalline tetraol 6. Attempts at cyclization of 6 with catalysts and acidic media known to promote benzyl cation chemistry afforded incomplete cyclization or mixtures of the desired products and oligomers, with mass balances in the 20-50% range. As one example, exposure of 5 to polyphosphoric acid at 100° C. gave nearly quantitative conversion to 7. This result supports initial ionization at the central hydroxyl group.

When tetraol 6 was added to an NMR tube containing 1 M TfOD (deuterated triflic acid) in DCE-d₄ (deuterated dichloroethane), the fluorescent green solution exhibited very simple ¹H and ¹³C NMR spectra, displaying three unique hydrogens and six carbon signals for the major species in solution. These data support formation of the symmetrical 8,12-dihydro-4H-dibenzo[cd,mn]pyren-3a²-ylium cation (8). Density functional theory (DFT) computations on 8 support a $D_{3h}$ symmetrical structure, with predicted NMR chemical shifts in good agreement with experiment. The optical spectrum of 8 also supports this structure. NMR samples of cation 8 were stable for >24 h. As expected, exposure of the partly cyclized structure 7 to the same acidic reaction conditions led cleanly to 8.

Preparation of Dihydro And Tetrahydro[3]triangulenes

Figure 3:
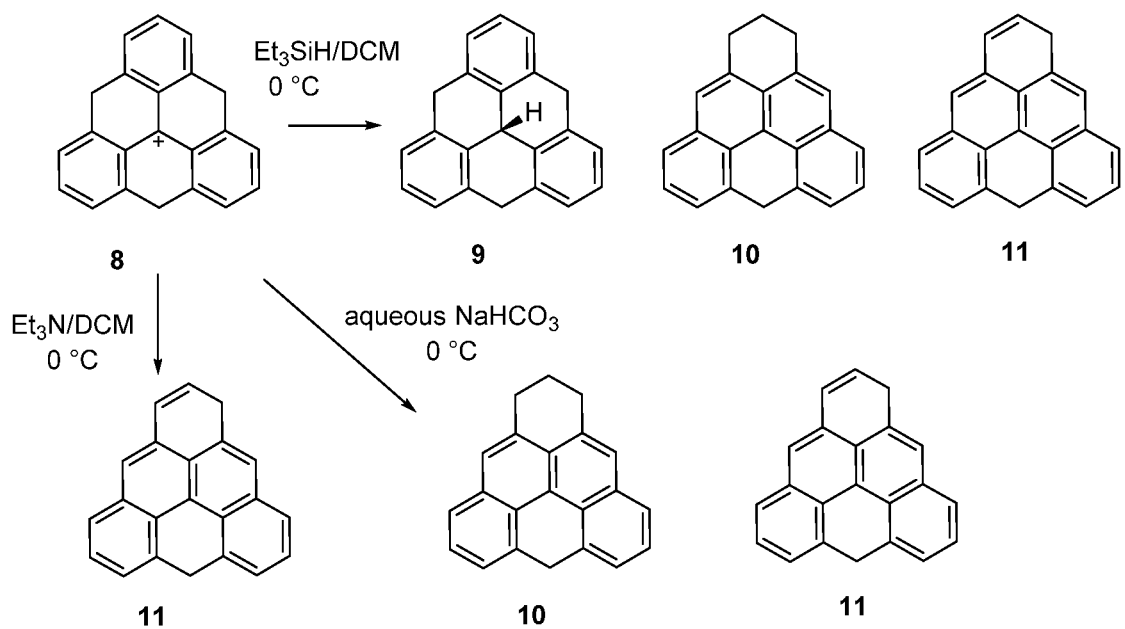
FIG. 3. Preparation of di- and trihydrotriangulenes from the 8,12-dihydro-4H-dibenzo[cd,mn]pyren-3a²-ylium cation.

After preparation of cation 8 by the method described above, neutralization by hydride transfer during slow addition to triethylsilane in DCM produced a mixture of hydrocarbons 9-11 in 96% isolated yield. See FIG. 3 Neutralization of 8 by addition to saturated aqueous NaHCO₃ afforded a mixture of compounds 10 and 11, while slow addition to Et₃N gave a 66% isolated yield of pure compound 11.

See Table 1 below.

TABLE 1

Synthesis of Dihydro and Tetrahydro[3]triangulenes

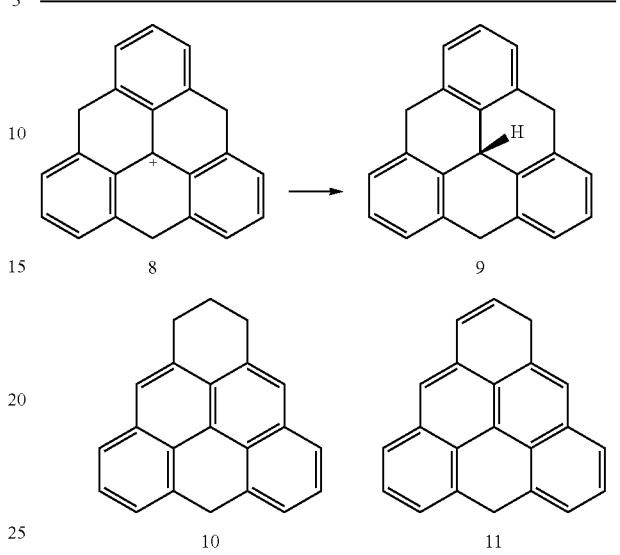

|  | 9 | 10 | 11 | Total Yield |
|---|---|---|---|---|
| Et₃SiH/DCM 0° C. | 38 | 9 | 49 | 96% |
| sat. NaHCO₃ 0° C. | — | 27 | 53 | 80% |
| Et₃N/DCM 0° C. | — | — | 66 | 66% |

The three compounds 9, 10 and 11 were separable by chromatography, providing pure samples of each hydrocarbon. Dihydrotriangulene 11 has been described previously as a precursor to compound 2[26] and its dianion[13] but was prepared according to the earlier synthetic route of Clar. The spectral data match those reported. 1,2,3,8-Tetrahydrotriangulene 10, is believed to be a new derivative of olympicene,[27] but with one additional saturated ring. Isomeric tetrahydrotriangulene 9 is also believed to be a new substance, characterized by its NMR spectra. The central methine hydrogen in 9 appears as a quartet (J=5.5 Hz) in the NMR because of long range coupling to the pseudoaxial methylene hydrogens. ⁵J Homoallylic coupling has been described previously in 1,4-cyclohexadienes.[28]

EXPERIMENTAL 1-((allyloxy)methyl)-2-bromobenzene (4

To an oven-dried 500 mL flask purged with nitrogen and cooled to 0° C. was added NaH (60% w/w, 7.04 g, 176 mmol) and anhydrous THF (50 mL) to give a grey suspension. A solution of 2-bromobenzyl alcohol (16.4 g, 88 mmol) in anhydrous THF (126 mL) was added dropwise via addition funnel and sonicated at 0° C. for 1 hr. Allyl bromide (15.2 mL, 176 mmol) was added dropwise then the mixture was sonicated at room temperature overnight to give a chalky white suspension. This was cooled to 0° C., quenched with water, extracted with DCM, washed with brine, dried with MgSO₄, gravity filtered, and condensed to give an orange oil. This oil was purified via vacuum distillation to give the desired product as a colorless oil (19.4 g, 97% yield, bp 58° C. at 0.17 torr). ¹H NMR (500 MHz, CDCl₃): δ 7.56-7.51 (m, 2H), 7.32 (td, J=7.53, 1.18 Hz, 1H), 7.17-7.12 (m, 1H), 6.00 (ddt, J=17.21, 10.43, 5.55 Hz, 1H), 5.37 (dq, J=17.24, 1.65 Hz, 1H) 5.27-5.23 (m, 1H), 4.60 (s, 2H), 4.13

(dt, J=5.56, 1.44 Hz, 2H); $^{13}$C NMR (500 MHz, CDCl$_3$): δ 137.8, 134.6, 132.6, 129.1, 128.9, 127.5, 122.7, 117.3, 71.8, 71.48.

tris(2-((allyloxy)methyl)phenyl)methanol (5

To an oven-dried 500 mL flask purged with nitrogen was added a solution of 1-((allyloxy)methyl)-2-bromobenzene (4) (18.3 g, 81 mmol) in anhydrous THF (208 mL) and the mixture was cooled to −78° C. n-BuLi (2.5 M, 35.6 mL, 89 mmol) was added dropwise over 30 min and the mixture was stirred at −78° C. for 1 hour to give a pale yellow solution. Freshly distilled diethyl carbonate (3.28 mL, 27 mmol) was added dropwise followed by stirring at −78° C. for 1 hour to give a bright orange solution. This was heated to 50° C. and stirred over night to give a yellow suspension. The crude product was cooled to 0° C., quenched with sat. aqueous NH$_4$Cl, extracted with DCM, dried with MgSO$_4$, gravity filtered, and condensed to give an orange oil. The impurities were removed by vacuum distillation to give the desired product as a viscous orange oil (12.05 g, 95% yield). $^1$H NMR (500 MHz, CDCl$_3$): δ 7.65 (d, J=6.70 Hz, 3H), 7.33 (td, J=7.49, 1.23 Hz, 3H), 7.09 (td, J=7.69, 1.33 Hz, 3H), 6.68 (d, J=7.67 Hz, 3H), 6.33 (s, 1H), 5.79 (ddt, J=17.16, 10.56, 5.31 Hz, 3H), 5.17 (dq, J=17.24, 1.62 Hz, 3H), 5.10 (dq, J=10.40, 1.33 Hz, 3H), 4.64 (d, J=13.21, 3H), 4.39 (d, J=13.23, 3H), 3.81 (dddt, J=41.37, 12.70, 5.58, 1.37 Hz, 6H); $^{13}$C NMR (126 MHz, CDCl$_3$): δ 144.6, 138.2, 134.4, 129.9, 129.0, 127.8, 126.8, 117.0, 85.5, 71.3, 71.0; HRMS (ESI/Q-TOF) m/z: [M+Na]+ Calcd for C$_{31}$H$_{34}$O$_4$Na 493.2355; Found 493.2351.

((hydroxymethanetriyl)tris(benzene-2,1-diyl)) trimethanol (6

To an oven-dried 250 mL flask purged with nitrogen was added Pd(PPh$_3$)$_4$ (0.049 g, 0.04 mmol) and MeOH (50 mL). A solution of tris(2-((allyloxy)methyl)phenyl)methanol (5) (2.0 g, 4.2 mmol) in MeOH (67 mL) was added followed by stirring at room temperature for 15 min. K$_2$CO$_3$ (10.5 g, 75.6 mmol) was added and the yellow suspension was heated to reflux. After 1 hour, a second equivalent of Pd(PPh$_3$)$_4$ was added and this process was repeated twice more for a total of four equivalents (0.196 g, 0.17 mmol, 4 mol %). The mixture was stirred at reflux overnight to give a yellow suspension. This was cooled to room temperature, condensed to remove MeOH, washed with sat. aqueous NH$_4$Cl, extracted with DCM, and flushed through a silica plug with ethyl acetate. The filtrate was condensed to give an orange slurry, which was dissolved in a minimum volume of DCM, then hexane was added to give a white precipitate. This was vacuum filtered and rinsed with cold hexane to give the desired product as a white solid (1.02 g, 69% yield, mp 182-184° C.). $^1$H NMR (400 MHz, DMSO-d$_6$): δ 7.69-7.62 (m, 3H), 7.33 (td, J=7.50, 1.18 Hz, 3H), 7.16 (s, 1H), 7.09 (td, J=7.74, 1.30 Hz, 3H), 6.56 (d, J=7.73 Hz, 3H), 5.31 (t, J=5.26 Hz, 3H), 4.34 (ddd, J=52.82, 14.18, 4.90 Hz, 6H); $^{13}$C NMR (101 MHz, DMSO-d$_6$): δ 143.48, 141.71, 128.03, 128.03, 127.44, 126.04, 84.99, 62.11; HRMS (ESI/Q-TOF) m/z: [M+Na]+ Calcd for C$_{22}$H$_{22}$O$_4$Na 373.1400; Found 373.1404.

((1,3-dihydroisobenzofuran-1,1-diyl)bis(2,1-phenylene))dimethanol (7

To a 50 mL flask was added water (2.8 mL), PPA (0.28 mL) and DCE (20 mL). The colorless solution was heated to reflux and a solution of ((hydroxymethanetriyl)tris(benzene-2,1-diyl))trimethanol (6) (0.100 g, 0.28 mmol) in DCE (8 mL) was added carefully followed by refluxing overnight (18 hours). The resultant opaque solution was cooled to room temperature, diluted with water, extracted with DCM, dried with MgSO$_4$, gravity filtered, and condensed to give pure the spirocycle 7 as an off-white solid (0.093 g, 97% yield, mp 126-130° C.). NMR (400 MHz, CDCl$_3$): δ 7.51 (d, J=7.12 Hz, 2H), 7.40-7.27 (m, 5H), 7.14 (td, J=7.66 1.42 Hz), 6.89 (d, J=7.52 Hz, 1H), 6.83 (d, J=7.63 Hz, 2H) 5.10 (s, 2H), 4.38 (s, 4H), 2.96 (s, 2H) $^{13}$C NMR (101 MHz, CDCl$_3$): δ 142.67, 141.46, 140.27, 138.84, 131.63, 128.84, 128.38, 128.06, 127.65, 127.22, 124.96, 121.39, 96.26, 70.64, 63.84; HRMS (ESI/Q-TOF) m/z: [M+Na]+ Calcd for C$_{22}$H$_{20}$O$_3$Na 355.1310; Found 355.1311

8,12-dihydro-4H-dibenzo[cd,mn]pyren-3a$^2$-ylium cation (8

To a nitrogen-flushed NMR tube was added a solution of ((hydroxymethanetriyl)tris(benzene-2, 1-diyl))trimethanol (6) (0.018 g, 0.05 mmol) in 1,2-dichloroethane-d$_4$ (1.0 mL) and triflic acid-d (0.09 mL, 1.0 mmol) to give a dark green solution. This was identified as the 8,12-dihydro-4H-dibenzo[cd,mn]pyren-3a$^2$-ylium cation. The same results were observed when using these reaction conditions on internally cyclized product (7) and tetrahydrotriangulene (9). $^1$H NMR (400 MHz, 1,2-dichloromethane-d$_4$): δ 8.11 (t, J=7.65 Hz, 3H), 7.89 (d, 7.71 Hz, 6H), 5.03 (s, 6H); NMR (101 MHz, 1,2-dichloromethane-d$_4$): δ 147.03, 139.25, 128.96, 123.32, 120.16, 116.99, 113.83, 36.93. UV-VIS λ$_{max}$ 404.5, 463, 5 (sh) nm.

Synthesis of 3a$^2$,4,8,12-tetrahydrodibenzo[cd,mn] pyrene (9

To an oven-dried 100 mL flask purged with nitrogen was added ((hydroxymethanetriyl)tris(benzene-2,1-diyl)) trimethanol (6) (0.058 g, 0.16 mmol) and DCM (33 mL) to give a colorless solution. Triflic acid (2.9 mL, 32.8 mmol) was added turning the solution dark green. This was transferred to an addition funnel and slowly added to a solution of triethylsilane (10.0 mL, 62.6 mmol) in DCM (28 mL) over 30 min at 0° C. to give a yellow solution. Water was added (100 mL) to give a bright yellow-green solution. The mixture was extracted with DCM, dried over MgSO$_4$, gravity filtered, and condensed to give a yellow oil. The crude product was purified by CombiFlash (100% hexanes) to afford 1,2,3,8-tetrahydrodibenzo[cd,mn]pyrene (10) (0.004 g, 9% yield), 1,8-dihydrodibenzo[cd,mn]pyrene (11) (0.022 g, 49% yield), and tetrahydrotriangulene (9) as an orange solid (0.017 g, 38% yield). 3a$^2$,4,8,12-tetrahydrodibenzo[cd,mn]pyrene $^1$H NMR (400 MHz, CDCl$_3$): δ 7.25-7.23 (m, 9H), 7.21-7.63 (m, 1H), 4.18 (dd, J=18.08, 4.69 Hz, 3H), 4.06 (d, J=17.92); $^{13}$C NMR (101 MHz, CDCl$_3$): δ 135.61, 133.95, 126.75, 125.61, 36.43, 35.99; HRMS (EI+/Q-TOF) m/z: [M]+ Calcd for C$_{22}$H$_{16}$ 280.1252; Found 280.1255.

Synthesis of 1,2,3,8-tetrahydrodibenzo[cd,mn]pyrene (10

To an oven-dried 50 mL flask was added a solution of ((hydroxymethanetriyl)tris(benzene-2,1-diyl))trimethanol (6) (0.100 g, 0.28 mmol) in DCM (28 mL). TfOH (1.0 mL, 11.3 mmol) was carefully added and the resultant dark green solution was stirred at room temperature for 5 minutes. This was transferred to an addition funnel and slowly added to a solution of sat. NaHCO$_3$ (100 mL) at 0° C. over the course of 30 min to give a dark green solution. This was extracted with DCM, dried with MgSO$_4$, gravity filtered and condensed to give a dark green solid. The crude product was purified by CombiFlash (100% hexanes) to afford tetrahydrotriangulene 10 as a bright yellow solid (0.021 g, 27% yield) and 1,8-dihydrodibenzo[cd,mn]pyrene (11) as a bright yellow solid (0.041 g 53% yield). 1,2,3,8-tetrahydrodibenzo[cd,mn]pyrene (10) $^1$H NMR (500 MHz, CDCl$_3$): δ 7.66-7.63 (m, 2H), 7.57 (s, 2H), 7.49-7.45 (m, 2H), 7.39 (dq, J=7.15, 1.45 Hz, 2H), 4.94 (s, 2H), 3.24-3.18 (m, 4H), 2.16-2.11 (m, 2H); $^{13}$C NMR (101 MHz, CDCl$_3$): δ 133.96, 133.25, 130.90, 126.48, 125.56, 125.34, 124.92, 123.90, 123.53, 123.44, 33.44, 31.06, 22.47; HRMS (ESI/FTMS) m/z: [M-H]+ Calcd for C$_{22}$H$_{15}$ 279.1170; Found 279.1172.

Synthesis of 1,8-dihydrodibenzo[cd,mn]pyrene (11

To an oven-dried 250 mL flask was added a solution of ((hydroxymethanetriyl)tris(benzene-2,1-diyl))trimethanol (6) (0.500 g, 1.4 mmol) in DCM (140 mL). TfOH (6.2 mL, 70 mmol) was carefully added over 20 minutes and the resultant dark green solution was stirred at room temperature for 5 minutes. This was transferred to an addition funnel and slowly added to a solution of triethylamine (19.5 mL, 140 mmol) in DCM (280 mL) at 0° C. over the course of 2 hours to give a brown-yellow solution. The reaction mixture was diluted with water (200 mL), extracted with DCM, dried with MgSO$_4$, gravity filtered, and condensed to give a brown solid. The crude product was purified by CombiFlash (100% hexane) to afford 1,8-dihydrodibenzo[cd,mn]pyrene as a bright yellow solid (0.256 g, 66% yield) estimated to be >95% pure by NMR. $^1$H NMR (400 MHz, CDCl$_3$): δ 7.64-7.58 (m, 3H), 7.45 (dt, J=13.16, 7.53 Hz, 2H), 7.40-7.33 (m, 3H), 6.74-6.69 (m, 111), 6.15 (dt, J=10.07, 4.01 Hz), 4.90 (s, 2H), 4.11 (s, 2H); $^{13}$C NMR (101 MHz, CDCl$_3$): δ 134.20, 134.13, 132.55, 132.14, 132.05, 130.47, 128.07, 127.91, 127.75, 126.98, 126.81, 126.63, 125.99, 125.47, 125.23, 125.03, 124.79, 124.52, 124.45, 123.25, 34.25, 31.91; HRMS (EI+/Q-TOF) m/z: [M]+ Calcd for C$_{22}$H$_{14}$ 278.1096; Found 278.1100.

REFERENCES

1. Kubo, T., Phenalenyl-Based Open-Shell Polycyclic Aromatic Hydrocarbons. *Chem. Rec.* 2015, 15 (1), 218-232.
2. Ratera, I.; Veciana, J., Playing with organic radicals as building blocks for functional molecular materials. *Chem. Soc. Rev.* 2012, 41 (1), 303-349.
3. Bearpark, M. J.; Robb, M. A.; Bernardi, F.; Olivucci, M., Molecular mechanics valence bond methods for large active spaces. Application to conjugated polycyclic hydrocarbons. *Chem. Phys. Lett.* 1994, 217 (5-6), 513-19.
4. Philpott, M. R.; Cimpoesu, F.; Kawazoe, Y., Geometry, bonding and magnetism in planar triangulene graphene molecules with D3h symmetry: Zigzag Cm**2+4m+1H3m+3 (m=2, . . . , 15). *Chem. Phys.* 2008, 354 (1-3), 1-15.
5. Gapurenko, O. A.; Starikov, A. G.; Minyaev, R. M.; Minkin, V. I., Carbon and silicon triangulenes: searching for molecular magnets. *Russ. Chem. Bull.* 2011, 60 (8), 1517-1524.
6. Das, A.; Muller, T.; Plasser, F.; Lischka, H., Polyradical Character of Triangular Non-Kekul'e Structures, Zethrenes, p-Quinodimethane-Linked Bisphenalenyl, and the Clar Goblet in Comparison: An Extended Multireference Study. *J. Phys. Chem. A* 2016, 120 (9), 1625-1636.
7. Sharma, V.; Som, N.; Dabhi, S. D.; Jha, P. K., Tailoring the Electronic and Magnetic Properties of Peculiar Triplet Ground State Polybenzoid "Triangulene". *ChemistrySelect* 2018, 3 (8), 2390-2397.
8. Toader, A. M.; Buta, C. M.; Frecus, B.; Mischie, A.; Cimpoesu, F., Valence Bond Account of Triangular Polyaromatic Hydrocarbons with Spin: Combining Ab Initio and Phenomenological Approaches. *J. Phys. Chem. C* 2019, 123 (11), 6869-6880.
9. Clar, E., Structure of aromatic hydrocarbons. *Chimia* 1964, 18 (12), 375-86.
10. Clar, E.; Stewart, D. G., Aromatic hydrocarbons. LXVIII. Triangulene derivatives. II. *J. Am. Chem. Soc.* 1954, 76, 3504-7.
11. Clar, E.; Stewart, D. G., Aromatic hydrocarbons. LXV. Triangulene derivatives. *J. Am. Chem. Soc.* 1953, 75, 2667-72.
12. Allinson, G.; Bushby, R. J.; Paillaud, J.-L.; Thornton-Pett, M., Synthesis of a derivative of triangulene; the first non-kekulé polynuclear aromatic. *J. Chem. Soc., Perkin Trans. 1* 1995, (4), 385-390.
13. Hara, 0.; Tanaka, K.; Yamamoto, K.; Nakazawa, T.; Murata, I., The chemistry of phenalenium systems. XXV. The triangulenyl dianion. *Tetrahedron Lett.* 1977, (28), 2435-6.
14. Inoue, J.; Fukui, K.; Kubo, T.; Nakazawa, S.; Sato, K.; Shiomi, D.; Morita, Y.; Yamamoto, K.; Takui, T.; Nakasuji, K., The First Detection of a Clar's Hydrocarbon, 2,6,10-Tri-tert-Butyltriangulene: A Ground-State Triplet of Non-Kekule Polynuclear Benzenoid Hydrocarbon. *J. Am. Chem. Soc.* 2001, 123 (50), 12702-12703.
15. Wang, Q.; Li, J.; Nie, Y.; Xu, F.; Yu, Y.; Wang, B., Pure spin current and phonon thermoelectric transport in a triangulene-based molecular junction. *Phys. Chem. Chem. Phys.* 2018, 20 (23), 15736-15745.
16. Sharma, V.; Dabhi, S. D.; Shinde, S.; Jha, P. K., Tuning electronic properties of graphene nanoflake polyaromatic hydrocarbon through molecular charge-transfer interactions. *AIP Conf. Proc.* 2018, 1961 (1), 030031/1-030031/6.
17. Mou, Z.; Kertesz, M., Sigma-versus Pi-Dimerization Modes of Triangulene. *Chem.— Eur. J.* 2018, 24 (23), 6140-6147.
18. Jin, H.; Li, J.; Wang, T.; Yu, Y., Photoinduced pure spin-current in triangulene-based nano-device. *Carbon* 2018, 137, 1-5.
19. Rosenberg, M.; Santella, M.; Bogh, S. A.; Vinas Munoz, A.; Andersen, H. O. B.; Hammerich, O.; Bora, I.; Lincke, K.; Laursen, B. W., Extended triangulenium ions—syntheses and characterization of benzo-bridged dioxa- and diazatriangulenium dyes. *J. Org. Chem.* 2019, Ahead of Print.
20. Hernandez Delgado, I.; Pascal, S.; Besnard, C.; Voci, S.; Bouffier, L.; Sojic, N.; Lacour, J., C-Functionalized Cationic Diazaoxa Triangulenes: Late-Stage Synthesis and Tuning of Physicochemical Properties. *Chemistry* 2018.
21. Nakatsuka, S.; Gotoh, H.; Kinoshita, K.; Yasuda, N.; Hatakeyama, T., Divergent Synthesis of Heteroatom-Centered 4,8,12-Triazatriangulenes. *Angew. Chem., Int. Ed.* 2017, 56 (18), 5087-5090.
22. Bogh, S. A.; Simmermacher, M.; Westberg, M.; Bregnhoej, M.; Rosenberg, M.; De Vico, L.; Veiga, M.; Laursen, B. W.; Ogilby, P. R.; Sauer, S. P. A.; Soerensen, T. J., Azadioxatriangulenium and Diazaoxatriangulenium: Quantum Yields and Fundamental Photophysical Properties. *ACS Omega* 2017, 2 (1), 193-203.

23. Hammer, N.; Schaub, T. A.; Meinhardt, U.; Kivala, M., N-Heterotriangulenes: Fascinating Relatives of Triphenylamine. *Chem. Rec.* 2015, 15 (6), 1119-1131.
24. Bosson, J.; Gouin, J.; Lacour, J., Cationic triangulenes and helicenes: synthesis, chemical stability, optical properties and extended applications of these unusual dyes. *Chem. Soc. Rev.* 2014, 43 (8), 2824-2840.
25. Field, J. E.; Venkataraman, D., Heterotriangulenes-Structure and Properties. *Chem. Mater.* 2002, 14 (3), 962-964.
26. Pavlicek, N.; Mistry, A.; Majzik, Z.; Moll, N.; Meyer, G.; Fox, D. J.; Gross, L., Synthesis and characterization of triangulene. *Nat. Nanotechnol.* 2017, 12 (4), 308-311.
27. Mistry, A.; Moreton, B.; Schuler, B.; Mohn, F.; Meyer, G.; Gross, L.; Williams, A.; Scott, P.; Costantini, G.; Fox, D. J., The Synthesis and STM/AFM Imaging of Olympicene Benzo[cd]pyrenes. *Chem.—Eur. J.* 2015, 21 (5), 2011-2018.
28. Durham, L. J.; Studebaker, J.; Perkins, M. J., Long-range coupling in the proton magnetic resonance spectra of 1,4-dihydrobenzenes. *Chem. Commun. (London)* 1965, (19), 456-7.

The invention claimed is:
1. A method for the preparation of 8,12-dihydro-4H-dibenzo[cd,mn]pyren-3a²-ylium cation comprising:
reacting an allyl-protected benzyl alcohol having the following structure:

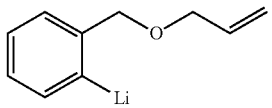

with diethyl carbonate to form tris(2-((allyloxy)methyl)phenyl)methanol having the following structure:

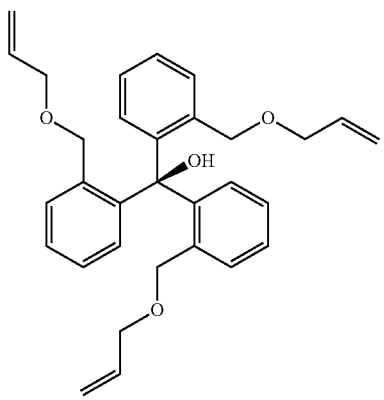

deprotecting said tris(2-((allyloxy)methyl)phenyl)methanol in the presence of a palladium catalyst to produce ((hydroxymethanetriyl)tris(benzene-2,1-diyl))trimethanol having the following structure:

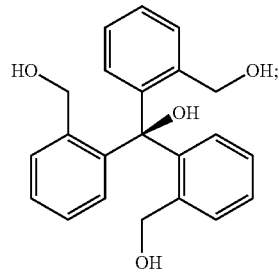

converting by cyclization said ((hydroxymethanetriyl)tris(benzene-2,1-diyl))trimethanol in the presence of triflic acid to produce the 8,12-dihydro-4H-dibenzo[cd,mn]pyren-3a²-ylium cation having the following structure:

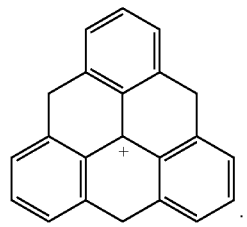 [SMILES: c1cc2c3c(c1)Cc1cccc4c1[C+]3c1c(cccc1C4)C2]

2. The method of claim 1 wherein said 8,12-dihydro-4H-dibenzo[cd,mn]pyren-3a²-ylium cation is converted by contacting with Et₃SiH/DCM at 0° C. to produce 3a²,4,8,12-tetrahydrodibenzo[cd,mn]pyrene having the following structure:

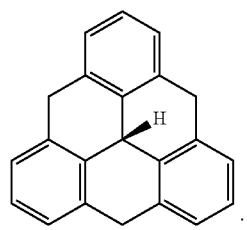

3. The method of claim 1 wherein said 8,12-dihydro-4H-dibenzo[cd,mn]pyren-3a²-ylium cation is converted by contacting with Et₃SiH/DCM or NaHCO₃ at 0° C. to produce 1,2,3,8-tetrahydrodibenzo[cd,mn]pyrene having the following structure:

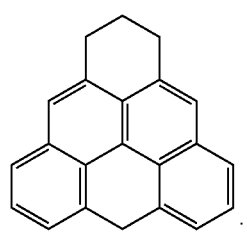 [SMILES: c1cc2c3c(c1)cc1c4c(cc5cccc(c5c43)C2)CCC1]

4. The method of claim 1 wherein said 8,12-dihydro-4H-dibenzo[cd,mn]pyren-3a$^2$-ylium cation is converted by contacting with Et$_3$SiH/DCM or NaHCO$_3$ or Et$_3$NDCM at 0° C. to produce 1,8-dihydrodibenzo[cd,mn]pyrene having the following structure:
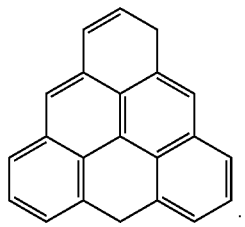 [SMILES: C1=Cc2cc3cccc4c3c3c2c(cc2cccc(c23)C4)C1]
* * * * *

UNITED STATES PATENT AND TRADEMARK OFFICE
CERTIFICATE OF CORRECTION

| | |
|---|---|
| PATENT NO. | : 11,236,029 B2 |
| APPLICATION NO. | : 16/876582 |
| DATED | : February 1, 2022 |
| INVENTOR(S) | : Richard Peter Johnson and Carter J. Holt |

It is certified that error appears in the above-identified patent and that said Letters Patent is hereby corrected as shown below:

In the Specification

In Column 1, Line 10, before "FIELD" insert:
--STATEMENT REGARDING FEDERALLY SPONSORED RESEARCH OR DEVELOPMENT
This invention was made with government support under 1362519 awarded by the National Science Foundation. The government has certain rights in the invention.--

Signed and Sealed this
Twenty-first Day of May, 2024

Katherine Kelly Vidal
*Director of the United States Patent and Trademark Office*